United States Patent [19]

Barsky et al.

[11] Patent Number: 5,643,787
[45] Date of Patent: *Jul. 1, 1997

[54] ADENOCARCINOMA CELL BASEMENT MEMBRANE COMPOSITION

[75] Inventors: Sanford H. Barsky; Mark Sternlicht, both of Los Angeles, Calif.

[73] Assignee: The Regents of the University of California, Oakland, Calif.

[*] Notice: The term of this patent shall not extend beyond the expiration date of Pat. No. 5,508,188.

[21] Appl. No.: 381,384

[22] Filed: Jan. 31, 1995

Related U.S. Application Data

[63] Continuation-in-part of Ser. No. 184,720, Jan. 21, 1994, Pat. No. 5,508,188.
[51] Int. Cl.$^6$ .................... C12N 5/00; C12N 5/02
[52] U.S. Cl. .................... 435/371; 435/378; 435/373; 435/395; 435/383; 435/391; 435/366
[58] Field of Search ................. 435/172.3, 240.1, 435/371, 240.2, 373, 240.21, 240.25, 391; 424/93.1

Primary Examiner—Deborah Crouch
Attorney, Agent, or Firm—Flehr Hohbach Test Albritton & Herbert LLP

[57] ABSTRACT

Methods and compositions are provided for the culture of human primary carcinomas and in situ carcinomas. Feeder layers derived from a human parotid basal cell carcinoma, having the HMS-1 phenotype, are able to support the growth of the primary carcinomas, and allow for spheroid formation. Invasion inhibiting factors active against human tumors, derived from HMS-1, are also provided.

Human basement membrane and extracellular matrix is provided, produced by a tumorigenic cell line, where the basement membrane and extracellular matrix can be used for the growth of a variety of cells, in culture and in vivo. Other related cell lines are provided, which can serve to evaluate in vivo the response of tumorigenic cells to various agents, including basement membrane and extracellular matrix. The basement membrane and extracellular matrix finds use in allowing the growth of cells in culture and in vivo, particularly cells which are otherwise refractory to xenografting.

10 Claims, No Drawings

ADENOCARCINOMA CELL BASEMENT MEMBRANE COMPOSITION

This is a continuation-in-part of application Ser. No. 08/184,720 filed Jan. 21, 1994, now U.S. Pat. No. 5,508,188 issued Apr. 16, 1996.

INTRODUCTION

1. Technical Field

The field of this invention relates to the in vitro culture of human myoepithelial and epithelial cells.

2. Background

Myoepithelial cells are thought to exert important paracrine effects on normal epithelial morphogenesis and mitogenesis in vivo through direct cell-cell interactions and through synthesis of a basement membrane extracellular matrix. Basement membranes are ubiquitous structures which are thought to be synthesized by several normal cell types including epithelial, endothelial, smooth muscle, Schwawn cells, and their derivatives. The transformed malignant counterparts of these latter cells, carcinomas and sarcomas, generally lose their ability to synthesize basement membranes and instead acquire basement membrane-degradative properties via the secretion of different families of proteases including metalloproteinases, serine proteinases and thiol proteinases.

Primary human carcinomas and carcinomas in situ also arise in the setting of surrounding myoepithelial cells, therefore it is probable that similar paracrine effects are exerted on carcinoma mitogenesis, morphogenesis, and progression, including tumor invasion and metastasis by these surrounding myoepithelial cells. Studies designed to investigate tumor cell interactions with basement membranes have relied heavily upon utilizing matrix derived from the unusual non-metastasizing Engelbreth-Holm, Swarm ("EHS") tumor. The EHS tumor matrix is rich in laminin, type IV collagen, nidogen and heparin sulfate proteoglycan, as well as the small matrix glycoprotein BM-40. These molecules have been extracted individually and as an unfractionated extract which reconstitutes to form a three-dimensional gel ("Matrigel") containing entrapped growth factors. This reconstituted basement membrane has been used extensively to study cellular differentiation, tumor cell invasion, angiogenesis and tumorigenicity. The coinjection of tumor cells and matrigel enables the in vivo growth of several otherwise non-tumorigenic cells and greatly stimulates the growth of a wide variety of primary and established tumor cells of both human and murine origin. However, matrigel has failed to support the growth of many primary human cancers, including prostatic and breast carcinoma. This is probably due to the failture of matrigel to recapitulate in vitro the paracrine relationship which exists in vivo.

Many experimental studies of human breast, prostate, and other cancers are based on studies with established cell lines, such as MCF-7, T47D, and MDA-MB-231. The vast majority of these cell lines are derived from metastatic foci, transplanted as xenografts in mice, and serially passaged in cell culture. As a result, these lines contain many genetic changes, including mutations, rearrangements and amplifications, which no longer accurately reflect the changes responsible for cancer progression in vivo. Furthermore, these cell lines are derived from metastatic foci, thereby reflecting advanced stages of tumor progression which could mask earlier steps of the process.

Investigators have been unable to derive new cell lines from primary carcinomas and pre-cancerous lesions, especially from the breast and prostate, despite the widespread occurrence of these diseases. Initially it was believed that the growth of contaminating fibroblasts present within the adjacent stroma was the cause of the difficulty in culturing such primary carcinomas. However, the development of selective media that inhibits the growth of fibroblasts, has not proven to be more successful.

It is therefore of interest to determine whether the synthesis of human basement membrane extracellular matrix, and interaction with human myoepithelial cells can be exploited to culture human primary and in situ carcinomas, and to determine factors involved in such interactions.

3. Relevant Literature

Barsky et al. (1988) *Cancer* 61:1798–1806 screened a series of human tumors by anti-laminin ELISA and discovered salivary gland adenoid cystic carcinoma to exhibit the highest amounts of human native extracellular matrix molecules. See also Ellis and Wiscovitch (1990) *Oral Surg. Oral Med. Oral Pathol.* 69:461–469 and Chudhry et al. (1986) *Cancer* 58:72–82. Myoepithelial cells are reported to be a rich source of basement membrane material in vivo and are likewise thought to be the source of basement membrane material in these tumors. Caselitz et al. (1988) *Path. Res. Pract.* 183:386–394; Chudhry (1986), supra.; U.S. Pat. Nos. 4,829,000 and 5,158,874; and International Application WO91/15245 describe the preparation of Matrigel and its use in determining metastatic potential of tumor cells, and growing tumor cells.

A number of investigators have established immortalized salivary gland carcinomas in culture which have manifested both a myoepithelial phenotype and matrix production either constituitively or through experimental induction. The salivary gland squamous cell carcinoma cell line HSG, described in Shirasuna et al. (1981) *Cancer* 48:745–752, has been shown to undergo both stable and reversible differentiation to myoepithelial, acinar and keratinizing squamous cell phenotypes, see Azuma et al. (1988) *Cancer Res.* 48:7219–7225; Yoshida et al. (1986) *Cancer* 57:1011–1018; Shirasuna et al. (1986) *Cancer Res.* 46:1418–1426; Sato et al. (1987) *Cancer Res.* 47:4453–4459; Hatakayama et al. (1987) *Acta Pathol. Jpn.* 37:587–595; Shirasuna et al. (1989) *Virchows Archiv B Cell Pathol.* 57:175–180; Iga et al. (1989) *Cancer Res.* 49:6708–6719 and Hayashi et al. (1988) *Cancer* 60:1000–1008.

Treatment of HSG cells with retinoic acid induced their reversible differentiation to a keratinizing squamous phenotype (Azuma, 1988). Manipulations which induced myoepithelial differentiation were: subcloning after 5-azacytidine treatment (which also yielded a stable acinar cell-like clone), treatment of cells with sodium-butyrate or dibutyryl cyclic AMP, coculture with normal human fibroblasts or their conditioned medium, or simple repeated single cell subcloning of the parent HSG line. Myoepithelial differentiation was accompanied by a substantial loss of tumorigenicity in nude mice, and those few tumors which did form resembled non-matrix producing myoepitheliomas (Azuma et al. (1986) *Cancer Res.* 46:770–777 and Shirasuna, 1988).

Human embryonal carcinoma cell lines have also been observed to differentiate with various in vitro manipulations, reviewed in Andrews (1988) *Biochim Biophys Acta* 948:17–36, and to secrete extracellular matrix molecules. Little else has been described, however, regarding the regulation of extracellular matrix production in these human tumor cell lines. Furthermore, no paracrine effects of these lines on the growth and morphogenesis of human carcinomas has been demonstrated.

SUMMARY OF THE INVENTION

Methods and compositions are provided for the culture of human epithelial cells, particularly primary carcinomas and in situ carcinomas. Feeder layers of myoepithelial cells derived from human salivary gland tumors are able to support the proliferation and epithelial morphogenesis of the epithelial cells. The myoepithelial cells actively produce an extracellular matrix, and factors which regulate the morphogenesis, mitogenesis and invasiveness of epithelial cell carcinomas.

A human basement membrane and extracellular matrix composition ("humatrix") is also provided, which comprises the protein components of human basement membrane and extracellular matrix in a three-dimensional scaffold. Humatrix finds use in the growth of human tumor cells, evaluation of metastatic potential of tumor cells, and as a source of the purified protein components. Humatrix can be obtained by extraction of the basement membrane and extracellular matrix from a xenograft of the subject myoepithelial cells.

The term "Humatrix" is intended to mean a human basement membrane-like, extracellular matrix composition comprising at least the major constituents of naturally occurring human extracellular matrix, where various growth factors may or may not be present. The ratios of the components will be about ±10% from the average of the naturally occurring tumoral basement membrane and extracellular matrix. The composition will at least comprise chondroitin sulfate proteoglycan, heparan sulfate proteoglycan, type I and IV collagen, laminin, and nidogen/entactin, usually also including fibronectin and $\beta$-tubulin.

DESCRIPTION OF THE SPECIFIC EMBODIMENTS

Human myoepithelial cells having the ability to regulate in vitro the proliferation, morphogenesis and invasiveness of epithelial cells, particularly primary carcinomas, are provided. The myoepithelial cells actively produce extracellular matrix, and regulatory factors. The subject myoepithelial cells are grown as immortalized cell lines, or as continuous xenografts. The xenograft produces large quantities of a human basement membrane-like extracellular matrix composition ("humatrix"), which comprises the protein components of human basement membrane and extracellular matrix in a three-dimensional scaffold. Humatrix finds use in the growth of human tumor cells, evaluation of metastatic potential of tumor cells, and as a source of the purified protein components. The immortalized myoepithelial cell lines are useful as feeder/regulatory layers in epithelial cell culture, and as a source of purified factors.

The subject myoepithelial cells are derived from human salivary gland tumors, and may be basal cell carcinoma or adenoidcystic carcinoma cells. The cells demonstrate genetic stability during continuous passage in synthetic media, or as a xenograft in a suitable immunocompromised animal. They may be further characterized by dependence on extracellular matrix, e.g. basement membrane, for tumorigenicity. The cells express high levels of maspin, a protease inhibitor, and human $\beta$-tubulin. Exemplary of the subject cells is the cell line HMS-1 and its xenograft counterpart, HMS-X. HMS-1 has been deposited at the American Type Culture Collection, at 12301 Park Lawn Drive, Rockville, Md. 20852, USA, on Jan. 12, 1995 and given the designation ATCC CRL-11792. HMS-X has been deposited with the ATCC, at 12301 Park Lawn Drive, Rockville, Md. 20852, USA, on May 25, 1995, and given the accession no. CRL-11899.

The subject compositions, both feeder layers and basement membrane/extracellular matrix, are biologically active in being able to support the growth in vitro of epithelial cells, particularly their transformed counterparts, carcinomas. Carcinomas of particular interest are primary, i.e. non-metastatic, and carcinoma in situ, i.e. a carcinoma in which all of the cytological and pathological criteria of malignancy are met, but which has not yet invaded surrounding tissue. Carcinomas include adenocarcinomas and adenoidcystic carcinomas that arise at various sites in the body, e.g. breast, salivary gland, pancreas, prostate, ovaries, squamous cell carcinomas of the skin and lung, basal cell carcinomas, e.g. skin, small cell lung carcinomas, colorectal carcinomas, melanomas, and the like. Usually the carcinomas will be human, although other mammalian cells may find use. It is known that human breast carcinomas and prostatic cancers are particularly difficult to grow in vitro and as xenografts.

The epithelial cells which are employed may be fresh tissue, usually obtained from patient biopsy, or freshly frozen tissue which was frozen within about 12 hours of removal from the patient and stored at below about $-10°$ C., usually at about liquid nitrogen temperature ($-70°$ C.). They may be fetal, neonatal or adult. Of particular interest are patient biopsy and surgical specimens from primary carcinomas. A cell suspension will be made from the solid tissue. It is usually not necessary to separate the carcinoma cells from surrounding tissue, however it may be desirable when employing non-transformed epithelial cells. Various methods are known in the art for separation of cell populations, including magnetic beads, cytotoxic agents, affinity chromatography, panning, fluorescence activated cell sorting, etc.

To support the growth and morphogenesis of epithelial cells in vitro, a feeder layer of myoepithelial cells is used. It is desirable that the initial growth of the feeder layer be in serum-free media, as HMS-1 cells undergo growth arrest at lower cell density, a change in growth pattern to island morphology, and ultimately terminal differentiation when cultured in the presence of serum. A number of defined serum-free media are known in the art. A monolayer of the subject myoepithelial cells is grown on an appropriate glass or plastic substrate, preferably until substantially confluent. Conveniently, tissue culture plates, e.g. 96 well plates, etc. or flasks may be employed where confluent cell layers may be maintained for extended periods of time without passage. In most cases the feeder layer will be treated to prevent further cell division, without killing the cells. Usually at least about 95% of the feeder layer cells will incapable of cell division, more usually at least about 98%. Such treatment may comprise irradiation, colchicine treatment, etc.

The epithelial cells are grown by placing onto the feeder layer, preferably in direct contact with the feeder layer cells. The cells may be grown at a relatively high density, for example, a suspension of about $10^4$ to $10^5$ cells/ml, or may be plated at limiting dilution. The media employed in the culture may be any convenient growth medium, such as RPMI-1640, IMDM, etc. either individually or in combination, where appropriate antibiotics to prevent bacterial growth and other additives, such as pyruvate (0.1–5 mM), glutamine (0.5–5 mM), 2-mercaptoethanol ($1-10\times10^{-5}$M) and from about 5–15% of serum, e.g. fetal calf serum. The cultures will remain viable for an extended period of time, usually at least about one week, more usually at least about 2 weeks, and may remain viable for at least about 4 weeks.

Under the subject growth conditions, primary carcinomas undergo active mitogenesis. The cells further undergo epithelial morphogenesis as evidenced by the formation of spheroids, which are reflective of the paracrine myoepithelial interactions present in vivo. Spheroid formation is defined as three dimensional formation of clusters of cells recapitulating a glandular or spheroidal shape. The spheroid is usually attached focally to the underlying feeder layer but can also be more broadly attached or become separated as it grows. Spheroids consist of a wide number of individual cells ranging from 10–1000. Spheroids can be first noted when they are very small, usually after at least about 2 to 4 days of culture. The epithelial cells may be passaged by division of the spheroids, or by disaggregation of the spheroids through EDTA, trypsin, dispase-collagenase, etc.

The subject cell cultures are useful for the diagnosis of primary tumors, and for the investigation of agents affecting primary carcinoma growth. Biopsy samples that cannot otherwise be grown in vitro can be cultured using the subject methods, providing cells for characterization as to genotype, invasiveness, drug sensitivity, etc. The ability of the feeder layers to induce morphogenesis allows further identification of genes and factors active in the paracrine regulation of epithelial cells by myoepithelial cells. For example, agents may be added to the subject cultures and assayed for activity in the disruption of paracrine interactions. Alternatively, the feeder layer cells may be manipulated to over- or underexpress various factors required for epithelial morphogenesis.

A disperse monolayer, i.e. lacking interepithelial junctions between cells, of the subject myoepithelial cells is able to regulate the invasive behavior of metastatic carcinomas by the production of factors that inhibit invasion. The monolayer of myoepithelial cells does not present a physical or mechanical barrier to invasion. The in vitro interaction is useful for the identification and study of factors useful as anti-invasive therapeutics.

A convenient assay for invasion measures the ability of metastatic cells to invade amnion. Subconfluent, rapidly growing metastatic cells are labeled with a suitable detectable label, e.g. radioactivity, fluorescence, etc. Amnions dissected from normal placentas are immobilized in soft agar. The epithelial layers may be denuded to expose the epithelial layer. The labeled tumor cells are added to the immobilized amnion, usually at least about $10^4$, more usually at least about $10^5$ cells, in serum-free medium with added fibronectin and laminin to promote attachment and added plasminogen to promote proteolysis via plasminogen activator. The cells are placed on the amnion surface and initially allowed to attach. After incubation for at least about 12 hours, usually at least about 24 hours, unattached cells are removed by washing. The cells attached to the surface of the amnion are lysed and removed. The detectable label still associated with amnion and soft agar layers is reflective of the number of invasive cells.

The presense of a monolayer of the subject myoepithelial cells inhibits invasiveness detected by the amnion assay by at least about 50%, and by as much as 95%. The invasion assay provides a means of evaluating factors and other agents active in the inhibition of invasion. Of particular interest is the expression of protease inhibitors, e.g. TIMP-1, maspin, etc. by myoepithelial cells that inhibit metastasis.

The growth regulatory ability of the subject myoepithelial cells is lost when the cells are fused to a metastatic cell line, e.g. C8161, and the like. After fusion, the hybrid cells do not support the growth of primary carcinomas, and will not inhibit invasion by metastatic cells. Such hybrid cells are useful as a negative control for growth and invasion assays, and for the identification of regulatory factors.

cDNA is made from HMS-1 and from (HMS-1×C8161) hybrids for differential screening and isolation of genes regulating the morphogenesis, growth and invasiveness of epithelial cells. Differential screening is used to identify protease inhibitors and other factors that are anti-invasive, proteins that mediate morphogenesis, and mitogenic factors.

Total RNA is isolated from HMS-1 and from (HMS-1× C8161) hybrids. Residual DNA may be removed in accordance with conventional techniques and the polyadenylated RNA purified further, on oligo-dT sepharose, gel chromatography, etc. cDNA may then be prepared in accordance with conventional techniques using reverse transcriptase (see Sambrook, et al., infra). The cDNA is then introduced into an appropriate cloning system, such as λ phage, pUC19, etc. The cDNA libraries are compared by +/− screening, subtractive hybridization, as described in U.S. Pat. No. 5,189,147, differential display, representational difference analysis (RDA), as described in PCT/US93/10722, genomic mismatch scanning, as described in U.S. Pat. No. 5,376,526, etc The cDNA inserts are then subcloned into other vectors, as desired. The cDNA may be used for further probing of the cDNA library for a complete transcript. Alternatively, the cDNA sequence may be used to probe a genomic library to identify the genomic gene encoding the subject proteins (See, for example, Molecular Cloning: A Laboratory Manual, 2nd ed., J. Sambrook, E. F. Fritsch, T. Maniatis, CSHL, Cold Spring Harbor, N.Y., 1989).

The subject DNA includes the nucleotide sequences encoding the specific proteins, as well as adjacent 5' and 3' non-coding nucleotide sequences involved in the regulation of expression of the protein encoded by the genes, and includes up to about the length of the mature mRNA. Also included in the corresponding genomic sequence are introns, and up to 1 kb of flanking genomic DNA at either the 5' or 3' end, and as much as 10 kb of flanking genomic sequence. These non-coding sequences include terminator and polyadenylation sequences, regulatory protein binding sequences, transcriptional regulatory sequences, and the like.

The nucleic acid compositions of the subject invention may be genomic or cDNA sequences encoding all or a part of the subject regulatory factors. Fragments may be obtained of the cDNA or genomic sequence by chemically synthesizing oligonucleotides in accordance with conventional methods, by restriction enzyme digestion, by PCR amplification, etc. For the most part, fragments will be of at least 12 nt, more usually at least 18 nt.

The DNA sequences may be obtained in substantial purity, and will be obtained as a sequence other than a sequence of an intact chromosome. Usually, the DNA will be obtained substantially free of other nucleic acid compounds, generally being at least about 50%, usually at least about 90% pure and are typically "recombinant", i.e. flanked by one or more nucleotides with which they are not normally associated with on a natural chromosome.

The DNA sequences may be used in a variety of ways. They may be used as probes for identifying related factors in the same, or other species. Homologous sequences are those with substantial sequence similarity, i.e. at least 80%, preferably at least 90%, more preferably at least 95% sequence identity with the nucleotide sequence. Such homologous nucleic acid sequences will be detected by hybridization under low stringency conditions, for example, at 50° C. and 10XSSC (0.9M saline/0.09M sodium citrate) and remain bound when subject to washing at 55° C. with 1XSSC.

The DNA may also be used to identify cells or organs which are expressing the subject genes. The manner in which one probes cells for the presence of particular nucleotide sequences, particularly as DNA, mRNA or cDNA, is well-established in the literature and does not require elaboration here. Conveniently, mRNA may be isolated free of DNA, and by using reverse transcriptase and PCR with specific primers, the subject cDNAs may be expanded, separated on gel electrophoresis and then probed using Southern blotting or sequencing. Other techniques may also find use.

For expression, the DNA sequences may be inserted into an appropriate expression vector, where the native transcriptional initiation region may be employed or an exogenous transcriptional initiation region, i.e. a promoter other than the promoter which is associated with the gene in the normally occurring chromosome. The promoter may be introduced by recombinant methods in vitro, or as the result of homologous integration of the sequence into a chromosome. A wide variety of transcriptional initiation regions are known for a wide variety of expression hosts, where the expression hosts may involve prokaryotes or eukaryotes, particularly E. coli, B. subtilis, mammalian cells, such as CHO cells, COS cells, monkey kidney cells, lymphoid cells, particularly human cell lines, and the like. Generally a selectable marker operative in the expression host will be present. The promoter may be operably linked to the coding sequence of the genes of interest so as to produce a translatable mRNA transcript. Expression vectors have convenient restriction sites located near the promoter sequence so as to provide for the insertion of nucleic acid sequences encoding heterologous proteins. The promoters in suitable expression vectors may be either constitutive or inducible. Expression vectors for the production of fusion proteins, where the exogenous fusion peptide provides additional functionality, i.e. increased protein synthesis, stability, reactivity with defined antisera, an enzyme marker, e.g. β-galactosidase, etc., are of particular interest.

Expression cassettes may be prepared comprising the transcription initiation region, which may be constitutive or inducible, with or without an enhancer sequence, including the endogenous or heterologous enhancer sequence, the gene encoding the subject factors or fragment thereof, and a transcriptional termination region, optionally having a signal for attachment of a poly A sequence. The gene may be genomic, including the native introns, or cDNA gene, or portion thereof. Of particular interest is the use of sequences which allow for the expression of functional epitopes, usually at least about 24 nucleotides in length, more usually at least about 48 nucleotides in length, and up to the complete open reading frame of the gene.

After introduction of the DNA, the cells containing the construct may be selected by means of a selectable marker, the cells expanded and then used for expression. Where secretion is desired, a signal peptide may be joined to the sequence, encoding the subject proteins or fragments thereof, whereby the protein will be expressed, translocated through the cell membrane, and processed to remove the signal peptide.

The expression cassettes may be introduced into a variety of vectors, where the vectors will normally be characterized by the ability to provide selection of cells comprising the expression vectors. The vectors may provide for extrachromosomal maintenance, particularly as plasmids in bacteria or viruses in eukaryotic cells, or for integration, particularly in mammalian cells. Where extrachromosomal maintenance is desired, an origin sequence will be provided for the replication of the plasmid, which may be a low- or high-copy plasmid. A wide variety of markers are available for selection, particularly those which protect against toxins, more particularly against antibiotics. The particular marker which is chosen will be selected in accordance with the nature of the host, where in some cases, complementation may be employed with auxotrophic hosts, e.g. yeast. Introduction of the DNA construct may be by any convenient means, e.g. calcium-precipitated DNA, electroporation, fusion, transfection, infection with viral vectors, etc.

Humatrix can be prepared by xenografting of the subject myoepithelial cell lines. Exemplary of a xenograft is HMS-X, which is related to HMS-1 and HMS-XC. Humatrix is particularly useful for the growth of epithelial cells as monolayers, and can provide for cell adhesion, growth and differentiation of a multiplicity of cells, including neurons, hepatocytes, sertoli cells, hair follicles, thyroid cells, and the like. Gene expression of most matrix molecules is considerably greater for HMS-X than for HMS-1 and HMS-XC, a cell line subsequently derived from HMS-X. Fibronectin gene expression shows the opposite pattern of gene expression, being 20-fold greater in HMS-1 than HMS-X. While the effects of serum on the extracellular matrix gene expression of HMS-1 mimic to some extent the expression noted in HMS-X, the expression is still both quantitatively and qualitatively different.

Depending upon the method of isolation, humatrix has in descending concentration: chondroitin sulfate proteoglycan, heparan sulfate proteoglycan, fibronectin, type I collagen, nidogen/entactin, laminin, type IV collagen (varies from about 1% of the naturally occurring amount to greater than about 100% of the naturally occurring amount, preferably about ±10% of the naturally occurring amount), and entrapped growth factors including TGF-β, EGF, bFGF, IGF-1, IGF-2, PDGF. These growth factors may be extracted from the gel, in whole or in part, their amounts may be enhanced, or additional factors added such as interleukins 1–15, colony stimulating factors, such as G-, M- or GM-; interferons, e.g. α, β or γ; erythropoietin, LIF, c-kit ligand, bone morphogenetic factors, NGF, or other factors that may find use in a particular application. For the most part, the entrapped growth factors will be present in a range of about 1 to 2 weight percent of the dry composition. Other factors, such as purified exogenous growth factors, particularly as described above, may be added to provide from about 2 to 5 weight percent, depending on the particular factor, the presence of other factors, the context in which Humatrix is being used, or the like.

For the most part, the chondroitin/heparan sulfate proteoglycan will be present in from about 15 to 35, more usually 20 to 30 weight %; fibronectin will be present in from 10–20% weight, the type I collagen will be present in from about 1 to 15 weight %, usually 2 to 10 weight %; the type IV collagen will be present in from about 1 to 15 weight %, usually from about 2 to 10 weight %; laminin will be present in from about 1 to 15 weight %, usually from about 2 to 10 weight %; nidogen/entactin will be present in from about 7.5 to 12.5 weight %, usually about 10 weight %; other minor proteins, such as BM90/fibulin, bamin, and BM40 will be present in from about 0.5 to 5 weight %, generally being present in total in from about 3 to 7 weight %, more usually a total of about 5 weight %. The remaining portion of the composition will include human β-tubulin and unknown components and will comprise not more than about 40 weight %, usually not more than about 30 weight %, and preferably not more than about 30 weight %. The subject composition will vary with the extraction method employed. With either method there will usually be less than about 40 weight % comprising presently unreported components.

Depending upon the manner of extraction, certain components in the Humatrix may vary. While for the most part, the sulfate proteoglycans and fibronectin will remain in about the same range, the type I collagen will on the average be in the range of about 2–5 weight % when extracting with urea/gdn-HCl, while about 5–10 weight % when using pepsin hydrolysis; the type IV collagen will generally be on the average in the range about 2–8 weight %, with urea/gdn-HCl, and about 1–5 weight % with pepsin hydrolysis; laminin will be present on the average in about 1–5 weight % with urea/gdn-HCl, and about 2–8 weight % with pepsin hydrolysis. The other characterized compounds will fall within the same ranges regardless of the manner of extraction. However, as already indicated the ranges may be changed by the addition of any of the components, although in the presence of the various components in solution, there appears to be a preferred ratio of the various components in the matrix.

It is found that the major basement membrane molecules (type IV collagen, laminin, nidogen and heparan sulfate proteoglycan) interact with one another and coprecipitate when combined in vitro. Depending upon the manner of isolation of Humatrix, type IV collagen may be underrepresented in the Humatrix composition. In order to provide for representative amounts of type IV collagen, the tumor bearing host must be rendered lathyritic, for example, with β-aminopropionitrile and a reducing agent employed during the extraction of Humatrix. In the absence of such agent, lower levels of type IV collagen are present. It is further found that the relative proportions (plus or minus 25% of the average proportion) of the reconstituted matrix molecules remains constant with various manipulations, indicating that the molecules interact in a stoichiometric manner. Humatrix resembles Matrigel in its overall structure and appearance at a grossly visible level, but differs from Matrigel at a molecular interactive level.

Humatrix is prepared at continually reduced temperature (4° C.) by repeated homogenization and centrifugation of HMS-X in a high salt solution containing protease inhibitors followed by overnight extraction in either a 6M urea, 2M guanidinium-HCl (gdn-HCl) buffer; or in a pepsin/acetic acid mixture. Salt concentrations will generally range from about 3.2 to 3.4M and the tumor explant will generally be homogenized at a ratio of 2 ml to 1 g in the salt solution. The final pellet obtained from the high salt extraction would generally comprise about from 40 to 70% of the original explant. This pellet will be mixed with 0.5 ml urea/gdn-HCl/g of starting material or 5 ml 0.5N acetic acid per g of starting material with 160 μl of freshly prepared 50 mg/ml pepsin in 0.01M HCl per g of starting material. The extraction process may be repeated, the supernatants combined and dialyzed against dilute aqueous chloroform (usually about 0.2 to 1%, more usually about 0.5% chloroform) using a dialysis membrane having a cutoff of 5–10 kDa. The temperature of the dialysis will generally be at about 0° to 10° C., usually 4° C., and the dialysis will be carried out for about 8 to 12 hr. After the dialysis with dilute aqueous chloroform, the supernatant will ordinarily be dialyzed against physiologic medium to make the product physiologically acceptable. Humatrix is preferably stored at −20° C., being a liquid at 4° C. and undergoes gelation at about 25°–37° C.

The subject human best basement membrane composition can replace Matrigel for its uses, particularly for human cells. It can be used as a coating for lab wear, where cells are to be grown in culture. It can be employed in a variety of tumor cell invasion assays (Taniguchi et al. (1989) *Cancer Research* 49:6738; Terranova et al. (1986) *Proc. Natl. Acad. Sci. USA* 83:465; Albini et al. (1987) *Cancer Research* 47:3239; and Hendrix et al. (1987) *Cancer Letters* 47:3239). The subject composition can support peripheral nerve regeneration, differentiation of epithelial cells, and may serve as a substrate for the study of angiogenesis. The subject membrane may be coated in a variety of ways where the Humatrix may be coated as a thin layer on a gel for plating cells on top of the gel, as a thick layer to allow for growth of cells within a three-dimensional matrix, or a thin coat, without gel, to provide a complex protein layer upon which cells may be grown. Generally, Humatrix will be used at a protein weight percent in the range of about 1 mg to 3 mg/ml, depending on the method of extraction. The subject composition may be used with cultures which are serum-free or contain serum.

The subject compositions can be used with cells for investigating the mechanisms of cell attachment, embryogenesis, morphogenesis, cell growth and differentiation, immunologic modulation, invasion and metastasis, as well as the role the basement membrane and extracellular matrix may play in a variety of diseases, as a result of pathogenesis, genetic defect, or the like. The subject membrane may also be used to investigate binding of a wide variety of factors to the basement membrane, the effect of the basement membrane on the activity of such factors, and the like.

The subject composition may be used in conjunction with a variety of cells to enhance the growth of the cells as xenoplants. All that is required, is that the cells, particularly human cells, are mixed in about a 1:1 volume ratio of cells to Humatrix and then injected into an appropriate host, particularly an immunocompromised host as described above. Thus, a wide variety of cells can be rapidly grown in an appropriate host.

Of interest, is the use of SCID-hu mice as described in EPA 88/312222.8; PCT/US91/02938; and EPA 91/113061.5. By providing for human tissue in the SCID-hu mouse, one can determine the metastatic potential of cells by determining whether the depot of tumor cells in the Humatrix composition metastasize to the human tissue. A wide variety of human tissue may be employed, such as bone marrow, bone marrow equivalent (see PCT/US93/04264), epithelial tissue, gut, pancreas, neural tissue, and the like.

In addition, one can study the effect of various agents on the growth of the tumor cells and the metastasis of the tumor cells in culture and in vivo. Thus, drugs may be employed for introduction into a culture medium or into a host at various concentrations, to determine the activity of the drug and its activity profile.

The following examples are offered by way of illustration and not by way of limitation.

EXPERIMENTAL

Materials and Methods

High molecular weight DNA was extracted from HeLa cells, HMS-1 cells, HMS-X, and nude mouse tissue by standard procedures using RNAase A, proteinase K, SDS and phenol (Sambrook et al., 1989, *Molecular Cloning: A Laboratory Manual, CSHL, NY*). The DNA was digested overnight at 37° C. with 14 units of HinfI or HaeIII per μg of DNA in the appropriate reaction buffer. Sodium acetate (pH 5.2) was then added to a 0.3M final concentration and the DNA was precipitated with ethanol. The recovered DNA was redissolved in TE (10 mM Tris, 1 mM EDTA; pH 8.0) and 3 µg of DNA were loaded onto each lane of a 24-cm-long, 1% agarose gel containing 0.3 µg/ml ethidium bromide. HindIII cut λ and HaeIII cut øX174 DNA molecular weight markers were run on both sides of the sample lanes. Electrophoresis was performed at 75 V for 16 hours in 1× TAE electrophoresis, the migration of DNA markers was determined by UV transillumination of the gel. For alkaline Southern transfer, gels were equilibrated in 0.4N NaOH, 0.6M NaCl for 30 minutes with agitation, and the denatured DNA was transferred overnight onto Nytran nylon membranes (Schleicher & Schuell, Keene, N.H.) by Southern capillary transfer in the same buffer. The membranes were neutralized in 5× SSC for 10 minutes and the DNA was immobilized by 254 nm UV crosslinking at 0.12 J/cm$^2$ of filter. Blots were stored desiccated at 4° C. between two sheets of Whatman 3MM paper and in plastic wrap.

The single-locus hypervariable probe pYNH24 was obtained from American Type Culture Collection (Rockville, Md.) in plasmid form (ATCC 57571). HB101 *E. coli* were rendered competent by suspension in 50 mM CaCl$_2$ and were transformed by standard methods (Sambrook et al., 1989, supra). Transformants were selected on LB agar plates containing 50 µg/ml ampicillin and were confirmed to contain the plasmid by restriction digest analysis of small-scale plasmid preparations. Plasmids were amplified in host *E. coli* grown overnight in LB culture medium supplemented with 50 µg/ml ampicillin at 37° C. in a gyrating water bath at 225 rpm. Plasmids were then recovered from large-scale cultures by alkaline lysis and purified by ethidium bromide-CsCl equilibrium centrifugation (Sambrook et al., 1989, supra). The 2.00 Kb insert was excised from pUC18 vector by sequential digestion with HindIII and EcoRI, and was isolated from a 1% low-melting-point agarose gel run in 1× TBE (90 mM Tris-borate, 2 mM EDTA; pH 8.0). Gel slices containing the insert were centrifuged for 5 minutes at 12,000 g and 5M NaCl was added to yield a 0.3M final concentration. After 1 hour at room temperature, the gel slices were melted at 65° C. for 10 minutes, and the DNA was extracted twice with 65° C. saturated phenol, further extracted twice with chloroform, precipitated with ethanol, and resuspended in TE. Twenty-five ng of insert were labeled with 50 µCi (3000 Ci/mmol) $\alpha^{32}$P-dCTP by random priming with a commercially available kit (Random Primers DNA Labeling System; BRL, Gaithersburg, Md.). Unincorporated nucleotides were removed from the radiolabeled probe by Sephadex G-50 spun column chromatography over TE Select-D, G-50 columns (5 Prime—3 Prime, Boulder, Colo.).

The multi-locus hypervariable probe 33.6 and a specific labeling primer were obtained from Cellmark Diagnostics (Germantown, Md.). Twenty ng of the probe were labeled with 50 µCi (3000 Ci/mmol) $\alpha^{32}$P-dGTP by primer extension as recommended by the supplier. Unincorporated nucleotides were removed from the radiolabeled probe by Sephadex G-50 spun column chromatography.

For some blots, the multi-locus probe 33.6 was obtained from a recombinant plasmid containing the 720 bp 33.6 DNA fragment. First, the vector pCRII (Invitrogen, San Diego, Calif.) was sequentially digested with HindIII and EcoRI. The released polylinker fragments were removed using a Select-D G-50 gel filtration column, and the vector was ethanol precipitated and resuspended in TE. Fifty ng of digested vector and 20 ng of 33.6 with EcoRI and HindIII sticky ends (Cellmark Diagnostics) were combined with T4 DNA ligase and the appropriate ligation buffer (Invitrogen), and ligation was allowed to proceed overnight at 12° C. Competent InvaF' *E. coli* were transformed with 1 µl of the ligation mixture according to the methods outlined by the supplier (Invitrogen). Recombinant clones were selected by ampicillin resistance and interruption of the LacZa gene which resulted in white colonies on LB agar plates containing 50 µg/ml ampicillin and 1 mg X-Gal. Presence of the recombinant plasmid was confirmed by restriction digest analysis of small-scale plasmid preparations on 1% agarose gels. Plasmid was then recovered from large-scale cultures by alkaline lysis and was purified by pZ523 spun column chromatography according to the methods recommended by the manufacturer (5 Prime—3 Prime). The 720 bp insert was released from the vector by sequential digestion with HindIII and EcoRI, and was isolated from a 1% low-melting-point agarose gel as described above for the pYNH24 insert. Twenty-five ng of gel isolated insert were labeled lay random priming and the radiolabeled probe was separated from unincorporated label as described above.

Nytran filters were placed in glass roller bottles and wetted briefly with deionized water. Nine ml of prewarmed QuikHyb hybridization solution (Stratagene, La Jolla, Calif.) were added, and the membranes were incubated at 68° C. in rolling hybridization oven for 30 minutes. One mg of sonicated salmon-sperm DNA and $12.5 \times 10^6$ cpm of $^{32}$P-labeled probe were combined and boiled for three minutes. One ml of prewarmed hybridization solution was then added to the boiled DNA and the mixture was transferred to the roller bottles and hybridization was carried out for 2 hours at 68° C. The membranes were washed twice with 2× SSC, 0.1% SDS at room temperature for 15 minutes with gentle agitation and then once with prewarmed 0.1× SSC, 0.1% SDS at 60° C. for 30 minutes in a rolling hybridization oven. The damp membranes were wrapped in plastic wrap and were exposed to Kodak X-OMAT AR film between two intensifying screens at −60° C. for 1 to 10 days. Blots which were stripped for reuse were washed twice for 15 minutes with near boiling 0.1× SSC, 0.1% SDS and were stored desiccated at 4° C. in plastic wrap.

Other probes designed to study constitutive matrix and protease inhibitor gene expression were prepared in similar fashion and applied to HMS-1 and HMS-X.

Gel Electrophoresis

The expression of a number of matrix molecule genes was shown using a cross-hybridizing murine cDNA probe for nidogen (Timpl (1983) *Eur. J. Biochem.* 137:455–465) and human cDNAs for the extracellular matrix molecules B1 and B2 chains of laminin (Timpl et al. *J. Biol. Chem.* 254:9933–9937), the A1 and A2 chains of type IV collagen (ATCC), the A1 chains of type I and type III collagen (ATCC), fibronectin, and the core proteins of a heparan sulfate proteoglycan (perlecan), Noonan et al., *J. Biol. Chem.* 266:22939–22947, and chondroitin sulfate proteoglycan. Matrix gene expression was studied with known probes to extracellular matrix molecules by polyA mRNA selection and extraction, followed by Northern blot gel electrophoresis, according to standard methods. (Sambrook et al., supra)

Establishment of Primary Prostatic and Primary Breast Carcinoma and Carcinoma in Situ Lines A series of cultures of primary prostate cancer including Gleason grades 1–5 are established from radical prostatectomy specimens. A series of cultures of primary breast carcinoma and carcinoma in situ (termed DCIS) from breast ductal carcinoma in situ are established from breast carcinoma biopsies. Prostatic carcinomatous areas are visualized by gross examination of the dissected gland and confirmed by frozen section. The area of the cancer is minced into 1 $mm^3$ fragments and subjected to overnight digestion in 10 ml of dissociating solution which consists of 200 units/ml of collagenase type I (Sigma, St. Louis, Miss.) plus 250 g/ml of DNA-ase type I (Sigma) dissolved in RPMI 1640 medium with 10% fetal calf serum. The fragments are digested at 37° C. with gentle agitation. The liberated cell clumps are washed, pelletized and resuspended in KGM selective media with added epidermal growth factor and bovine pituitary extract supplements (GIBCO, Grand Island, N.Y.). The growth of contaminating fibroblasts is suppressed with this media and only epithelial cells grow out of the clumps. After subsequent passage, the population is 100% epithelial which can be verified by positive keratin immunoreactivity and negative vimentin immunoreactivity. Flow cytometric studies are carried out on the cultured cells to determine ploidy.

Culturing on Humatrix and HMS-1

Pure populations of prostate and breast carcinoma cells, before they exhibit any signs of terminal differentiation (increased size or expression of high molecular weight keratins), are cultured on Humatrix or HMS-1. Humatrix and HMS-1 cultures are compared to cultures on plastic. The cells grown on Humatrix and HMS-1 are monitored with respect to their proliferation, their immunocytochemical profile, their DNA content, and their PSA secretion for prostate cells, or estrogen receptor levels for breast cells, as evidence of both their genetic as well as phenotypic stability. Specifically, the ability of Humatrix and HMS-1 to retard or prevent terminal differentiation in prostatic and breast carcinoma cells, and DCIS, which is inevitable when the cells are cultured on plastic is observed.

Proliferation Studies

Initial studies of proliferation include studies of cell culture doubling time. Subsequent studies use two standard approaches: Ki-67 antigen expression and bromodeoxyuridine uptake. A murine monoclonal antibody, Ki-67 (Dako Corporation) which recognizes an as-yet undefined human nuclear epitope present in cells in S, $G_1$, $G_2$, and M, but not $G_0$ is used to study the percentage of cells in the cultured prostatic carcinomas engaged in active proliferation. A second approach involves studies of bromodeoxyuridine uptake. The strategy employs 5-bromo-2'-deoxyuridine (BrdU), a thymidine analog, which is incorporated into replicating DNA and subsequently localized using a specific murine monoclonal antibody to BrdU (Amersham). Only cells in S phase of the cell cycle display nuclear immunoreactivity. The prostatic and breast carcinoma cells growing on Humatrix and HMS-1 are labeled. Prostatic and breast carcinoma cells are exposed to thymidine-free media supplemented with bromodeoxyuridine (3 g/ml) for 1-4 hours prior to immunocytochemical analysis.

Immunocytochemical Studies

Immunocytochemical studies employ the use of standard murine monoclonal or rabbit polyclonal antibodies to PSA for prostatic cells (1/50 dilution), antibodies to ER (estrogen receptor) for breast cells, low molecular weight (39, 43, 50 kd) cytokeratin (1/30 dilution); intermediate molecular weight (34βE12) (58, 56.5, 56 kd) cytokeratin (1/1000 dilution), vimentin (1/20 dilution), and smooth muscle actin (1/2000 dilution) (DAKO Corporation, Carpinteria, Calif.; Becton-Dickinson, Mountain View, Calif.). The second antibody used in the immunocytochemical studies is an affinity-purified peroxidase-conjugated sheep anti-mouse IgG or goat anti-rabbit IgG (1/200, 1/25 dilutions, respectively). Detection of immunocytochemical positivity is achieved by conjugating peroxidase polymerizing diaminobenzidine (DAB), producing brownish-black staining at sites of antigen presence. The expression of keratins in the prostatic carcinoma cells cultures on Humatrix and HMS-1 is monitored over time and compared to routine cultures. A switch in keratin expression, especially to higher molecular weight cytokeratins, suggests phenotypic instability or the beginnings of terminal differentiation.

Flow Cytometric Studies

For flow cytometric studies, a single nuclear suspension is obtained from monolayer cell cultures grown on either plastic, Humatrix or HMS-1 by trypsin digestion, and staining with propidium iodide in the presence of 0.1% Triton X-100, which cells are analyzed on a FACSCAN (Becton Dickinson Immunocytometry Systems, Mountain View, Calif.). The propidium iodide fluorescence histogram obtained from normal peripheral blood lymphocytes is used to standardize the location of the diploid peak, and additional gating of the forward scatter-side scatter dot plot is used to exclude the contribution of fragmented nuclei. The fluorescence histograms are then analyzed. Flow cytometry and DNA ploidy is used not only to screen the initial cultures but to monitor them over time for genetic stability/instability.

Karyotype Analysis

Karyotype analysis of the lines is carried out periodically by Giemsa-banded staining. The cells are split, plated in fresh media, allowed to attach for 8 hr, and exposed to 1 μM colchicine for 4-8 hr. For slower growing partner cells and their fusions, the length of colchicine exposure is lengthened to result in increased numbers of cells arrested in metaphase. After exposure the cells are harvested in 0.1% trypsin-EDTA. The cells are centrifuged at 3000 g for 10 minutes and the pellet resuspended in 0.035M KCl, 0.5% sodium citrate. The lysed cells are fixed in 2.0% paraformaldehyde for 10 minutes and drops titrated on a microscopic slide and allowed to air dry. The slides are stained with Giesma stain and the mitotic chromosomes examined in a Zeiss Photomicroscope III with a 63X plan-apo lens and an attached projection screen. The chromosomal spreads are optimized to reveal enough good metaphase preparations to count yet avoid the phenomenon of "chromosome soup". In optimal preparations, 20 chromosomal spreads are counted for each cell line. Mean, range, medium, and modal chromosomal number are calculated. Based predominantly on the modal numbers and ranges as well as the presence of marker chromosomes, whether the cultured prostate and breast carcinoma cells are manifesting genetic stability when cultured on Humatrix and/or HMS-1 compared to routine conditions is determined.

Prostatic Specific Antigen (PSA) Secretion Studies

Prostate cultures are monitored from time to time with respect to PSA secretion. Cells that are anticipated to undergo terminal differentiation after several passages on plastic are compared to cells grown on Humatrix and HMS-1. Prostatic carcinoma cells are seeded in plastic, Humatrix-coated 24 well plates ($10^6$ cells/well), and on feeder monolayers of HMS-1. After seeding the prostatic epithelial cells to uncoated and Humatrix-coated wells, and on feeder monolayers of HMS-1, and allowing them to attach and grow, conditioned media is collected for 24 hr every other day for 10 days and pooled. The pooled conditioned media is clarified and concentrated and cell number determined by trypsinizing the cells and counting in a Coulter Counter. PSA levels in conditioned media are determined using the Tandem-R PSA immunoradiometric assay (Kuriyama et al. (1980) Cancer Res. 40:4658–4666). For PSA, 50 μl of conditioned media is added to plastic tubes followed by monoclonal anti-PSA IgG-coated beads and 100 μl of $^{125}$I-labeled anti PSA IgG tracer antibody. The Tandem-R Assay is a solid phase, two-site immunoradiometric assay. Samples containing PSA are reacted with a plastic bead (solid phase) coated with a monoclonal antibody directed toward a unique site on the PSA molecule and, simultaneously, with a radiolabeled monoclonal antibody directed against a distinctly different antigenic site on the same PSA molecule. Following the formation of the solid phase/PSA/labeled antibody sandwich, the bead is washed to remove unbound labeled antibody. The radioactivity bound to the solid phase is measured in a gamma counter. The amount of radioactivity measured is directly proportional to the concentration of PSA present in the test sample, which is determined from a standard curve. The standard curve is based on the concurrent testing of the PSA calibrators from 0 to 100 ng PSA/ml. Using this assay, the samples are incubated for 4 hours, washed (2×) with phosphate-buffered saline and counted in a Picker gamma counter. Cultured prostatic carcinoma cells are monitored periodically for PSA secretion so as to determine their phenotypic stability in Humatrix and on feeder monolayers of HMS-1 compared to routine culture conditions. PSA secretion inevitably decreases when prostatic carcinoma cells are cultured on plastic as they undergo terminal differentiation.

Preparation of Humatrix a. Xenoplantation of tumor cells and growth of tumor

The tumor is serially passaged with a trochar. 1 mm$^3$ fragments are placed subcutaneously. Up to four fragments may be introduced into the mouse in the flank and back, in accordance with conventional procedures.

b. Extraction of Humatrix, isolation and characterization

1. Urea/guanidinium-HCl method: Tumors are harvested at 1–2 g of size. A given mouse can support the growth of 4 independent tumors. The tumor is grown in mice rendered lathyritic by feeding them a diet containing β-aminoproprionitrile (BAPN) fumarate. Approximately 10 g of tumor are harvested. Tumors are homogenized in 2 ml/g starting material of a high salt extraction buffer (3.4M NaCl, 0.05 Tris-HCl, 20 mM EDTA, 10 mM N-ethyl maleimide (NEM), pH 7.4) at 4° C. The homogenate is spun for 15 min at 12,000 g at 4° C. and the supernatant is discarded. The previous two steps are repeated twice more. The resulting pellet is extracted overnight at 4° C. with 0.5 ml urea/gdn-HCl extraction buffer per g starting material with stirring (6M urea, 2N gdn-HCl, 50 mM Tris-HCl, 20 mM EDTA, 10 mM NEM, pH 7.4 with added 2.0 mM dithiothreitol (DTT)). The extract is spun for 30 min at 24,000 g at 4° C. The supernatant is dialyzed against several changes of Tris buffered saline (TBS) at 4° C. (0.15M NaCl, 0.05M Tris-HCl, 20 mM EDTA, 10 mM NEM, pH 7.4). For sterilization, the final dialyses are against 0.5% chloroform, followed by physiologic cell culture media using a dialysis membrane with a cutoff of 5–10 kDa.

Using the above procedure, 0.5 ml of 3 mg/ml Humatrix is obtained from 1 g of HMS-X starting material. Humatrix can be stored frozen at −20° C., is a liquid at 4° C., and undergoes gelation at 25°–37° C. within 1 hr. The integrity of the formed gel is demonstrated by its being impervious to penetration by a loading dye composed of 12.5 g Ficoll, 0.125 g bromophenol blue and 0.125 g xylene cyanol.

2. Pepsin hydrolysis method: Tumors are harvested and homogenized in high salt buffer, the process repeated twice and a pellet obtained as described above. The mice need not be rendered lathyritic, and can be fed a normal diet. The pellet is suspended in 5 ml 0.5N acetic acid per g of starting material. 160 μl of freshly prepared 50 mg/ml pepsin in 0.01M HCl per g of starting material is added. Extraction occurs overnight at 4° C. with stirring. The extract is spun for 15 min at 3000 g at 4° C. The supernatant is removed and dialyzed against 50 mM Tris, 20 mM EDTA, 10 mM NEM, pH 7.8 overnight at 4° C. The leftover pellet is re-extracted and the steps repeated beginning with the suspension in acetic acid. The dialyzed supernatants are pooled and 240 mg solid NaCl/ml is added. The solution is stirred for 20 hr at 4° C., followed by centrifugation at 17,000 g for 30 min at 4° C. The pellet is resuspended in 0.5 ml 0.5N acetic acid with 20 mM EDTA and 10 mM NEM and dialyzed against several changes of 0.005N acetic acid, 0.14M NaCl, 5 mM KCl, 20 mM EDTA, and 10m mM NEM at 4° C. For sterilization purposes, the acetic acid substitutes for the chloroform, which was used in the previous extraction method. However, if the acetic acid proves toxic to certain cells, an additional dialysis against media can be used.

The resulting solution is concentrated to 0.25 ml final volume per g of starting material (or any volume which yields at least 1 mg/ml final protein concentration) by ultrafiltration at 4° C. (A microcon-10 microconcentrator with a 10 kDa molecular weight cut-off can be used; a centricon-10 could be used for larger amounts and a centriprep-10 for even larger volumes.)

Using the pepsin hydrolysis method, 0.25 ml of 1 mg/ml Humatrix is obtained from 1 g of HMS-X starting material. The product has the properties described for the urea/gdn-HCl preparation.

HMS-1 Growth and Culture

HMS-1 was established directly from a patient's tumor with histopathological features of a basal cell adenocarcinoma, a subtype of adenoidcystic carcinoma in keratinocyte growth media (KGM) (GIBCO, Grand Island, N.Y.) supplemented with manufacturer amounts of recombinant EGF and bovine pituitary extract. It was shown to be mycoplasma-free by direct culture in indirect Hoechst DNA staining, as well as by electron microscopy. The line exhibited immortality and a stable phenotype, having a stable karyotype and phenotype unchanged for over 100 passages with a population doubling time of approximately 24 h. The line is split from 1:3 to 1:5 with trypsin:EDTA. Antibodies specific for low molecular weight cytokeratins (39, 43, 50 kDa and smooth muscle actin (DAKO Corporation, Carpinteria, Calif.; Becton Dickinson, Mountain View, Calif.) showed the cells to be immunoreactive to these antibodies, indicating the myoepithelial nature of HMS-1. Employing antibodies specific for laminin and type IV collagen, approximately 30% of the cells were positively immunostained. Ultrastructural examination revealed microvilli and parallel arrays of microfilaments (thin filaments, dual structures of a myoepithelial phenotype). Monolayer cultures grown as described above reveal the presence of a scant basal extracellular electron dense matrix and the complete absence of cell-to-cell attachments (desmosomes).

In cultures comprising HMS-1 cells in the media described above to which 10% FCS was added, after 5–7 days, the cells underwent growth arrest at lower cell density than in the absence of FCS, a change in growth pattern to island morphology, and epithelial differentiation, which was reflected in the acquisition of numerous desmosomes. The cell line underwent terminal differentiation and serum after several doublings, which required 12–14 days.

Chromosome analysis of HMS-1 grown in the absence of serum carried out by Giemsa-banded staining of metaphase spreads at passages 2, 30 and 55 revealed an essentially diploid modal chromosome count of 46–47 (range 45–50). Common karyotypic changes were the loss of chromosomes 6 and 22, an abnormal chromosome 8q, and a rearranged marker chromosome, t(6;9) (p11.2; p13). There was also a gain of an extra chromosome 20 between passages 2 and 30. DNA ploidy analysis of several early passages (passage 2 days) and late passages (passage 30 days; passage 55 days) by flow cytometry confirmed the stable diploid nature of the line.

HMS-X Growth

Fresh tissue from the tumor supplying HMS-1 (1 mm$^3$ sized fragments were implanted subcutaneously via trochar into the flank and back of athymic nude mice (BALB/c). Mice were kept in aseptic housing in a laminar flow room. Bedding, food and water were all sterilized. When tumors reached 1–2 cm in greatest diameter, 1 mm$^3$ explants were passed to subsequent mice.

The original surgical specimen was a white to tan, multinodular mass exhibiting cylandromatous and cribriforming histologic patterns with abundant acellular matrix deposits as well as squamous metaplastic changes within invasion islands. The transplanted xenograft exhibits gross appearance similar to that of the original tumor as evidenced by gross, routine microscopic immunocytochemical staining and ultrastructural studies. The xenograft retained an abundant eosinophilic extracellular matrix which stained strongly with alcian blue and periodic acid-Schiff stains. The latter stain was shown to be diastase-sensitive by pre-digesting with diastase and abolishing staining supporting the presence of glycosylated matrix molecules other than mucin, e.g. proteoglycans. From earliest xenograft passage the extracellular matrix comprised approximately 50% of the tumor volume. The extracellular matrix exhibited strong immunoperoxidase staining for laminin. Electron microscopy revealed tumor cell islands surrounded by an abundant ground substance-like matrix which lack periodic cross-banded fibers and resemble the ultrastructural appearance of Matrigel (EHS) tumor matrix.

Results

DNA fingerprint profiles using single and multi-locus hypervariable probes (pYNH24 and 33.6) were identical for the xenograft in each of three passages of the cell line and demonstrated a novel band pattern differing from that of HeLa cells and a negligible DNA contribution from murine cells. There was no evidence of a murine DNA component by flow analysis, nor by the DNA fingerprint profiles, establishing the human origin of the cells.

The proteins being expressed were determined using cDNA probes for a number of basement membrane mRNAs. Gene expression of the matrix molecules: type IV collagen; type I collagen, heparan sulfate proteoglycan; chondroitin sulfate proteoglycan, nidogen and laminin including either 1, 2 or 3 chains was considerably greater for HMS-X, than for HMS-1 and HMS-XC, the primary exception being the fibronectin gene, being 20-fold greater for HMS-1 than HMS-X. A comparison of the in vitro effects of serum on extracellular matrix gene expression of HMS-1 compared to HMS-X was performed demonstrating that the expression between the two cells lines was still quantitatively and qualitatively different. Levels of extracellular matrix gene expression were determined by Northern blot gel electrophoresis and compared. HMS-X still expressed extracellular matrix transcripts at higher levels than serum-treated HMS-1 except for fibronectin and heparan sulfate proteoglycan.

Attempts to engraft HMS-1 in athymic (nude) or scid/scid mice failed. The cell line HMS-XC also failed to form tumors upon grafting in the same mice. HMS-X failed to grow xenografts after removal of the supporting extracellular matrix from the tumor explant by mechanical and enzymatic dissociation and subsequent reinjection of the washed cells, despite their ability to grow in culture.

The conclusion from these results is that HMS-X, HMS-1 and HMS-XC are obligately matrix dependent for their tumorigenicity. When HMS-1 was grown on the surface of Matrigel, glandular differentiation occurred; however, when HMS-1 was suspended 1:1 into liquid Matrigel according to manufacturer's recommendation and injected into athymic mice, no tumors emerged from 20 injection sites (5 mice) after periods of up to six months. However, when HMS-1 was mixed with Humatrix, there was a 40% rate of emerging tumors (tumorigenicity).

Further Characterization of the Myoepithelial Origin of HMS-1 and HMS-X

The actin and cytokeratin immunoreactivity indicated that HMS-1 and HMS-X were of myoepithelial origini. Ultrastructural examination revealed microvilli and parallel arrays of microfilaments (thin filaments), dual structures also supportive of a myoepithelial phenotype. Additional proof of the myoepithelial origin of HMS-1 and HMS-X and their stability is based on the findings of strong beta-tubulin immunoreactivity and extraction.

A conspicuous 55 kDa band was observed by SDS-PAGE in the 2M urea extracts of HMS-X and two related human salivary gland tumors, including an adenoidcystic carcinoma and pleomorphic adenoma, two tumors thought also to be of myoepithelial origin. This band was essentially absent from all other extracts tested, including those of normal salivary gland, placenta, kidney, cartilage, desmoplastic lung and breast adenocarcinomas, mucin, the murine EHS tumor and xenografts of the human melanoma cell lines C8161, M24 and A375 as well as a somatic cell hybrid of C8161 and HMS-1. The protein was absent from 3.4M NaCl extracts and showed identical electrophoretic migration under reducing and non-reducing conditions. Metabolic labeling with $^{35}$S-methionine also revealed considerable synthesis of the protein by HMS-X.

For amino acid sequence analysis, extracted proteins were separated by SDS-PAGE, transferred to PVDF membrane by electroblotting, stained with Coomassie blue, and the 55 kDa band excised for automated protein sequence analysis. The N-terminal sequence showed 94% identity to human beta-tubulin in 17 amino acid overlap. Immunolocalization studies using a monoclonal antibody against rat beta-tubulin (Zymed 08-0093) confirmed strong cytoplasmic immunoreactivity within basal cell adenocarcinoma, adenoidcystic carcinoma and pleomorphic adenoma. Other common salivary gland tumors including Warthin's tumor, mucoepidermoid carcinoma and acinar cell tumor were non or weakly immunoreactive.

Analysis of the adjacent normal salivary gland revealed the strongest beta-tubulin reactivity within myoepithelial cells and intercalated ductal epithelium with comparatively weak to non-immunoreactivity in adjacent excretory ductal and terminal acinar epithelium. Assuming comparative levels of beta-tubulin expression for adult salivary gland cells and their transformed counterparts, the findings further support the myoepithelial origin of HMS-1 and HMS-X.

Effects on Primary Carcinoma and Carcinoma in situ Morphogenesis

Feeder layers were prepared by gamma irradiation of 80–90% confluent cultures with 3000 rads. Dishes were irradiated in a GammaCell 1000 irradiator. 3000 rad doses were accomplished over approximately 10 min based upon the decay of the radiation source. Feeder layers were produced from HMS-1, normal human dermal fibroblasts (NHDF; Clonetics Corp.), MCF-7 breast carcinoma cells (ATCC) and early and late passage C8161 melanoma cells (F. Maskins and M. J. Hendricks). Human target cells were seeded atop each feeder cell type on the following day in their respective growth media. Target cells tested were HMS-1, primary cells from an adenoidcystic carcinoma of salivary gland origin, HMS-3, salivary gland epidermoid carcinoma cells (A253; ATCC HTB 41), MCF-7, MDA-MB-231 breast adenocarcinoma cells (ATCC HTB 26), 10 primary prostate carcinoma cultures, 10 primary breast carcinoma cell cultures, 5 breast carcinoma in situ (DCIS) cultures, and early (nonmetastatic) and late (metastatic) passage C8161 cells.

Spheroidal multicellular aggregates appeared at 2–4 days after seeding onto HMS-1 feeder layers for all primary prostate and breast carcinoma target cells as well as all breast carcinoma in situ cells tested. At approximately 1 week, florid spheroid formation was generally observed with up to 50 clusters per 10× objective field, some apparently containing several hundred cells. Spheroids did not form when these same target cells were grown on other feeder layers, as shown in Table 1. Spheroids also did not form when the target cells were established and immortalized cell lines derived from metastatic foci. 50% of the primary cultures eventually formed a glandular pattern with cell bridges linking adjacent spheroids. Spheroids that were trypsinized into individual cells and passed singly to new feeder layers reformed spheroid growth. Spheroids that were trypsinized intact, maintained their spheroid pattern and continued to grow when passed to new feeder layers of HMS-1. The results are shown in Table 1.

TABLE 1

| Target Cells | Spheroid Formation – Irradiated Feeder Cells | | | | |
|---|---|---|---|---|---|
| | none | HMS-1 | NDHF | MCF-7 | C8161 |
| HMS-1 | + | + | – | – | – |
| HMS-3 | – | + | ND** | ND** | ND** |
| A253 | – | – | – | – | – |
| MCF-7 | – | – | – | – | – |
| MDA-231 | – | – | – | – | – |
| 1° prostate cancer 1* | – | + | – | – | – |
| 1° prostate cancer 2* | – | + | – | – | – |
| 1° prostate cancer 3* | – | + | – | – | – |
| C8161 | – | – | – | – | – |

*The results depict 3 examples of individual cases of primary prostatic carcinomas.
**ND, not done.

Subsequent passages of carcinoma cells and carcinoma in situ cells grown on HMS-1 maintain their spheroid morphogenesis. The primary carcinomas and carcinomas in situ which grow as spheroids on HMS-1 grow only individually on plastic and do not exhibit spheroid formation. When grown on plastic, primary carcinoma and carcinoma in situ cells senesce or terminally differentiate and cease division after a few divisions. When grown on feeder layers of HMS-1, these same carcinoma cells form spheroids and continue to divide indefinitely. This spheroid and growth response is completely absent on Matrigel.

The observation of spheroid induction using HMS-1 as feeder layer is specific and reflective of the successful in vitro recapture of significant paracrine myoepithelial-epithelial interactions present in vivo. These interactions permit the successful culture and immortalization of fastidious human cell lines which, to date have not been able to be cultured by any other means.

Anti-Invasive Effects and Protease Inhibitor Expression of HMS-1

When HMS-1 was grown on a de-epithelialized human amnion, it exhibited dramatic anti-invasive effects on a number of different highly invasive human cell lines, including a series of human melanomas and human breast and prostate cancers derived from metastatic foci.

A series of ER positive (T47D, MCF-7, MDA-MB-175, 549, MDA-MB-157) and ER negative (MDA-MB-231 and Hs578T) human breast carcinoma and human melanoma (C8161) lines were chosen for study. Subconfluent (rapidly growing) breast carcinoma and human melanoma cells of these lines were labeled with [$^{125}$I]IdUrd (0.5 Ci [$^{125}$I] IdUrd/ml, specific activity 200 Ci/mmol) for 24 hours. Amnions were dissected from freshly delivered normal placentas and prepared under five different sets of experimental conditions: (1) amnions with an intact epithelial layer were clamped in a lucite holder, supported by soft agar, and $5 \times 10^5$ labeled tumor cells were added to the upper chamber; (2) the amnions were prepared as before except that their epithelial layers were denuded with 0.1% ammonium hydroxide, exposing their underlying basement membranes prior to the introduction of the labeled tumor cells; (3) the amnions were prepared undenuded and a monolayer of $5 \times 10^5$ HMS-1 cells were added 12 hours prior to the introduction of the labeled tumor cells; (4) the amnions were prepared denuded and a monolayer of $5 \times 10^5$ HMS-1 cells were added 12 hours prior to the introduction of the labeled tumor cells; (5) the amnions were prepared denuded with an added monolayer of HMS-1 which was then subject to irradiation to produce a feeder monolayer of HMS-1. While the addition of HMS-1 in all cases produced a confluent monolayer of cells, these cells lacked interepithelial junctions. Therefore, the confluent monolayer of HMS-1 did not present a mere physical or mechanical barrier to invasion.

Following the experimental set-up, $5 \times 10^5$ labeled carcinoma or melanoma cells of the various lines being studied were suspended in 2 ml of serum-free medium with added fibronectin (1 µg/ml) and added laminin (1 µg/ml) to promote attachment and added plasminogen (10 µg/ml) to promote proteolysis via plasminogen activator. The cells were placed on the amnion (0.76 cm$^2$) surface and initially allowed to attach for 90 minutes at 37° C. at 5% CO2 and then invasion assays were performed after 72 hours. At the end of the incubation, unattached cells were removed by gentle washing; cells attached to the surface of the amnion were lysed with 4% deoxycholate and removed with a rubber policeman. The amnion surface was washed and the radioactivity still associated with amnion and soft agar layers, reflecting the number of invasive cells, was determined with a gamma counter. The amnion and agar associated radioactivity was expressed as a total percentage of total radioactivity added to each amnion holder; results were expressed as mean ±S.D. and experiments were performed in quadruplicate.

Results

Human carcinoma and melanoma cell lines exhibited varying degrees of invasion of human amnion, but when an overlying monolayer of HMS-1 was present, invasion was significantly decreased in all cell lines tested, ranging from a 50 to 95% decrease. The effect of irradiation of HMS-1 producing a "non-dividing feeder" layer did not affect the ability of this layer to inhibit invasion.

As the anti-invasive process is mediated, in part, by protease inhibitors, HMS-1 and HMS-X were studied for the expression of protease inhibitors.

Of normal cells, the protease inhibitor maspin is expressed in greatest amounts in normal human myoepithelial cells. The gene sequence is described in Zou et al. (1994) Science 263:526–529. TIMP-1 (tissue inhibitor of metalloproteinases-1) is a common mesenchymal protease inhibitor. The gene sequence is described in Docherty et al. (1985) Nature 318:66–69 and Gasson et al. (1985) Nature 315:768–771.

Maspin mRNA expression was determined by northern blot analysis using a 1 kb maspin cDNA probe. The expression of TIMP-1 was also determined, using the 0.7 kb cDNA insert of pEPA. Poly-A selected mRNA (2–5 µg per lane) was separated on a 1% denaturing agarose gel, transferred to nylon membrane and hybridized with $^{32}$P-labeled probe. Protease inhibitor expression was examined for mRNA isolated from HMS-1, salivary gland epidermoid carcinoma cells (A253; ATCC HTB 41), normal human prostate derived fibroblasts (NHF), MDA-MB-231 breast adenocarcinoma cells (ATCC HTB 26), and a human diploid cell line derived from normal breast tissue adjacent to a desmoplastic infiltrating ductal carcinoma (Hs578Bst; ATCC HTB 125).

The 3.0 kb maspin transcript and a 1.6 kb band were readily detected in HMS-1 and HMS-X, but were completely absent from all other cells including normal fibroblasts. Maspin immunoreactivity has been found to be strong in normal myoepithelial and epithelial cells. When compared to normal breast myoepithelial and epithelial cells, maspin expression was almost 5 times greater in HMS-1 and 3.5 times greater in HMS-X. TIMP-1 expression was similar in HMS-1 and HMS-X and was approximately half that observed in normal human fibroblasts and Hs578Bst cells. HMS-1 and HMS-X are the first immortalized cell line and transplantable human xenograft demonstrated to express maspin. HMS-1 and HMS-X and the anti-invasive protease inhibitor prototype which they exhibit may be used to identify novel protease inhibitors characteristic of the myoepithelial phenotype.

Matrix Studies of HMS-X Involving Glycosaminoglycan Analysis

Glycosaminoglycans were extracted from cells and tissues as described by Nakanishi et al. (1992) Biochem J. 288:215–224 and were analyzed by the two-dimensional electrophoresis method of Hata and Nagai (1972) Anal. Biochem. 45:462–468. To estimate relative amounts of the respective glycosaminoglycans, alcian blue stained membranes were scanned and the integrated density of the glycosaminoglycan spots were determined using NIH Image 1.49. Glycosaminoglycan standard curves analyzed in this fashion were linear from 0.25 to 5 mg per spot (r=0.98). Hexuronate was measured by the colorimetric method of Bitter and Muir (1962) Anal. Biochem. 4:330–334 and DNA content was determined by the flurometric method of Downs and Wilfinger (1983) Anal. Biochem. 131:538–547. Chondroitin 4-sulfate (C4S), chondroitin 6-sulfate (C6S), dermatan sulfate (DS), heparan sulfate (HS), hyaluronic acid (HA), keratan sulfate (KS) and calf thymus DNA standards were purchased from Sigma Chemical Co. Glucuronolactone standards were obtained from Eastman Kodak Co.

The total uronic acid content and glycosaminoglycan composition of the various samples are given in Table 2. Total uronic acid levels were comparable for HMS-X and the murine tumor EHS. The uronic acid content of HMS-X was almost 6 times greater than normal salivary gland by tissue dry weight, and was 17-fold greater when normalized to cellular DNA content. CS was the predominant glycosaminoglycan in HMS-X, accounting for approximately 78% of the tumoral glycosaminoglycans. HMS-X also contained 12% HA, 8% HS and 2% DS. Normal salivary gland, by contrast, contained little CS (4%) and considerably more HA (56%), HS (24%) and DS (16%). EHS tumor contained mostly HS (94%) and some HA (6%). KS was not detected in any tissue sample.

Glycosaminoglycans were also analyzed for HMS-1. HMS-1 cells were harvested with a cell scraper so as to retain cell surface proteoglycans. The cells contained 32% CS, 12% HA, 24% HS and 32% KS. KS accounted for almost ⅓ of the cellular glycosaminoglycans yet was not detected in HMS-X, suggesting that it was exclusive to the cellular compartment. DS, on the other hand, was not detected in HMS-1, suggesting that the small amount of DS observed in HMS-X might be murine in origin, i.e. associated with the tumor capsule and septa. The DNA-normalized uronic acid content of HMS-1 was 1.5% that of HMS-X, indicating that the bulk of tumoral glycosaminoglycans were associated with the extracellular matrix compartment. However, since KS does not contain hexuronate, it is not represented in the uronic acid measurements, and these measurements underestimate the total glycosaminoglycan content of HMS-1 by about 32%. Thus, using DNA-normalized uronic acid measurements and correcting for the undetected KS in HMS-1, we calculate that approximately 2.2% of the glycosaminoglycans in HMS-X are cell- or cell surface-associated (0.7% CS, 0.3% HA, 0.5% HS and 0.7% KS) and the remaining 97.8% are matrix-associated (76.3% CS, 11.7% HA, 7.8% HS and 2% DS).

TABLE 2

Glycosaminoglycan Analysis

| Cell Type | Uronic Acid µg/µg DNA | Glycosaminoglycan Content (%) | | | | |
|---|---|---|---|---|---|---|
| | | CS | HA | HS | DS | KS |
| HMS-X | 0.530 | 78 | 12 | 8 | 2 | 0 |
| HMS-1 | 0.008 | 32 | 12 | 24 | 0 | 32 |
| Normal Salivary Gland | 0.031 | 4 | 56 | 24 | 16 | 0 |
| Murine EHS Tumor | 0.356 | 0 | 6 | 94 | 0 | 0 |

Therefore, clear cut qualitative and quantitative differences exist between the matrix compositions of the murine EHS tumor and the human HMS-X and HMS-1 cells.

Abolishment of HMS-1/HMS-X's Spheroid Induction, Maspin Expression and Matrix Production Cancer progression in vivo includes the acquisition of properties essential for metastasis. Whether the specific genes which regulate metastasis act dominantly (analogous to oncogenes) or recessively (analogous suppressor genes) is not known. Using an approach designed to circumvent earlier steps of tumor progression, somatic cell hybridizations were obtained with polyethylene glycol fusions between a human melanoma line, the C8161, which exhibits a high rate of spontaneous metastasis in scid/scid and nude mice, and HMS-1.

The hybrid cells (C8161×HMS-1) contained a full and stable chromosomal content (modal number of 128). There was complete abolishment of maspin transcription and extracellular matrix synthesis. The hybrid cell layer when grown as an irradiated feeder layer was not able to induce spheroid formation in either primary carcinomas or carcinomas in situ. The hybrid cells were fully metastatic in scid/scid mice.

These results demonstrate the presence of dominant-acting genes present in C8161 which are able to silence the expression of extracellular matrix and protease inhibitor proteins, and those proteins which regulate spheroid formation.

It is evident from the above results that novel immortalized myoepithelial cells can be provided that regulate the growth, morphogenesis and invasiveness of carcinomas. The subject cells are useful for the culture of fastidious human cells, particularly carcinoma biopsies and other primary tumors which have not been previously grown in culture. The carcinoma cultures are useful in the diagnosis of patient tumors, providing cells for drug sensitivity testing, karyotyping, assessment of invasiveness, and the like. The paracrine interactions between myoepithelial and epithelial cells can be studied in vitro with the subject cultures, and used to identify and isolate regulatory factors.

Novel human basement-like and extracellular matrix compositions are provided which may be used for a variety of purposes, such as studying interactions between extracellular matrix and cells, growing cells in culture and in vivo, extracting components individually or in combination from the basement membrane as a source of these components, and the like. Cells are provided that can be used for studying basement membrane and extracellular matrix component expression, response to various agents affecting the basement membrane and extracellular matrix expression, and the like.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A cellular composition comprising cells isolated from a human parotid basal adenocarcinoma, wherein said composition is selected from the group consisting of HMS-1 and HMS-X.

2. The composition according to claim 1, wherein said cells are HMS-1.

3. The composition according to claim 2, wherein said cells are grown as a monolayer.

4. The composition according to claim 1, wherein said cells are HMS-X.

5. A method of culturing human primary carcinoma cells or human breast ductal carcinoma in situ cells in vitro, the method comprising:

introducing said cells in vitro to a culture medium comprising a feeder layer of cells selected from the group consisting of HMS-1 and HMS-X; and culturing said cells under conditions for proliferation.

6. The method according to claim 5, wherein said human primary carcinoma cells are from primary breast carcinoma or primary prostate carcinoma.

7. The method according to claim 5, wherein said culturing causes said cells to form spheroids.

8. A basement membrane-like composition prepared from cells selected from the group consisting of HMS-1 and HMS-X, wherein the composition comprises from about 20 to 30 weight % heparin/chondroitin sulfate proteoglycan, from about 10 to 20 weight % fibronectin, from about 2 to 10 weight % type I collagen, from about 3 to 10 weight % type IV collagen, from about 2 to 10 weight % laminin and about 10 weight % nidogen/entactin.

9. The basement membrane-like composition according to claim 8, wherein said cells are grown as a xenograft.

10. A method for growing human tumorigenic cells in a non-human mammalian host, the method comprising introducing said tumorigenic cells mixed with a basement membrane like composition comprising from about 20 to 30 weight % heparin/chondroitin sulfate proteoglycan, from about 10 to 20 weight % fibronectin, from about 2 to 10 weight % type I collagen, from about 3 to 10 weight % type IV collagen, from about 2 to 10 weight % laminin and about 10 weight % nidogen/entactin into said mammalian host; and growing said mammalian host for sufficient time for said tumorigenic cells to grow.

* * * * *

UNITED STATES PATENT AND TRADEMARK OFFICE
CERTIFICATE OF CORRECTION

PATENT NO. : 5,643,787
DATED : July 1, 1997
INVENTOR(S) : BARSKY, et al.

It is certified that error appears in the above-identified patent and that said Letters Patent is hereby corrected as shown below:

Column 1, line 7, immediately preceding INTRODUCTION, insert a new paragraph to read --This invention was made with Government support under Grant No's.: CA 40225; CA 71195; CA 01351, awarded by the National Institutes of Health. The Government has certain rights in this invention.--.

Signed and Sealed this

Thirtieth Day of March, 1999

Attest:

Attesting Officer

Q. TODD DICKINSON

Acting Commissioner of Patents and Trademarks